US009528115B1

(12) United States Patent
Weller et al.

(10) Patent No.: US 9,528,115 B1
(45) Date of Patent: Dec. 27, 2016

(54) *PSEUDOMONAS FLUORESCENS*2-79 WITH GENES FOR BIOSYNTHESIS OF PYRROLNITRIN IMPROVES BIOCONTROL ACTIVITY

(71) Applicants: The United States of America, as represented by the Secretary of Agriculture, Washington, DC (US); Washington State University Research Foundation, Pullman, WA (US)

(72) Inventors: David M Weller, Pullman, WA (US); Linda S Thomashow, Pullman, WA (US); Dmitri V Mavrodi, Hattiesburg, MS (US); Mingming Yang, Xianyang (CN); Jibin Zhang, Wuhan (CN)

(73) Assignees: The United States of America, as represented by The Secretary of Agriculture, Washington, DC (US); Washington State University, Pullman, WA (US)

( * ) Notice: Subject to any disclaimer, the term of this patent is extended or adjusted under 35 U.S.C. 154(b) by 99 days.

(21) Appl. No.: 14/208,543

(22) Filed: Mar. 13, 2014

Related U.S. Application Data

(60) Provisional application No. 61/793,784, filed on Mar. 15, 2013.

(51) Int. Cl.
   *C12N 15/78* (2006.01)
(52) U.S. Cl.
   CPC .......... *C12N 15/78* (2013.01); *C12N 2510/02* (2013.01)
(58) Field of Classification Search
   None
   See application file for complete search history.

(56) References Cited

PUBLICATIONS

Mozes-Koch R et al. Expression of an Entire Bacterial Operon in Plants. 2012. Plant Physiology. vol. 158, pp. 1883-1892.*
Mavrodi DV et al. A Seven-Gene Locus for Synthesis of Phenazine-1-Carboxylic Acid by *Pseudomonas fluorescens*2-79. 1998. Journal of Bacteriology. vol. 180, No. 9. p. 2541-2548.*
Arima, Kei et al., "Pyrrolnitrin, a New Antibiotic Substance, Produced by Pseudomonas", (1964) Agricultural and Biological Chemistry 28(8):575-576.
Bull, Carolee, D. Weller and L. Thomashow, "Relationship between Root Colonization and Suppression of es graminis var. tritici by *Psaudomonas fluorescens*Strain 2-79", (1991) Phytopathology 81(9):954-959.
Chernin, Leonid et al., "Pyrrolnitrin Production by an Enterobacter agglomerans Strain with a Broad Spectrum of Antagonistic Activity Towards Fungal and Bacterial Phytopathogens", (1996) Current Microbiology 32:208-212.
Cook, R. James et al., "Yield Responses of Direct-Seeded Wheat to Rhizobacteria and Fungicide Seed Treatments", (2002) Plant Disease 86(7):780-784.
Cook, R. James et al., "Take-all of wheat", (2003) Physiological and Molecular Plant Pathology 62:73-86.
Delany, I.R. et al, "Enhancing the biocontrol efficacy of *Pseudomonas fluorescens*F113 by altering the regulation and production of 2,4-diacetylphloroglucinol", (2001) Plant and Soil 232:195-205.
El-Banna, N. and G. Winkelmann, "Pyrrolnitrin from Burkholderia cepacia: antibiotic activity against fungi and novel activities against streptomycetes" (1998) Journal of Applied Microbiology 85:69-78.
Fernando, W. G. D. et al., "Biological control of Sclerotinia sclerotiorum (Lib.) de Bary by Pseudomonas and Bacillus species on canola petals" (2007) Crop Protection 26:100-107.
Gurusiddaiah, S. et al., "Characterization of an antibiotic produced by a strain of *Pseudomonas fluorescens*inhibitory to Gaeumannomyces graminis var. tritici and Pythium spp." (1986) Antimicrobial Agents and Chemotherapy 29(3):488-495.
Hammer, Philip, E. et al., "Postharvest Control of Botrytis cinerea on t Rose Flowers with Pyrrolnitrin" (1993) Plant Disease 77:283-286.
Hammer, Phillip, E. et al., "Conservation of the pyrrolnitrin biosynthetic gene cluster among six pyrrolnitrin-producing strains" (1999) FEMS Microbiology Letters 180:39-44.
Hu, Xiaojia et al., "Decreased incidence of disease caused by Sclerotinia sclerotiorum and improved plant vigor of oilseed rape with Bacillus subtilis Tu-100" (2005) Applied Microbiology and Biotechnology 68:802-807.
Huang, Zhengyu et al., "Transformation of Pseudomonas fluorescens with genes for biosynthesis of phenazine-1-carboxylic acid improves biocontrol of rhizoctonia root rot and in situ antibiotic production" (2004) FEMS Microbiology Ecology 49:243-251.
Huber, D.M. et al, "Rhizoctonia Crown Rot of Canola in Indiana" (1992) Plant Disease 76:1251-1253.
Janisiewicz, W.J. and J. Roitman, "Biological Control of Blue Mold and Gray Mold on Apple and Pear with Pseudomonas cepacia" (1988) Phytopathology 78:1697-1700.
Kaminski, D.A. and P.R. Verma, "Cultural characteristics, virulence, and in vitro temperature effect on mycelial growth of Rhizoctonia isolates from rapeseed" (1985) Canadian Journal of Plant Pathology 7(3):256-261.
Kataria, H.R. and P.R. Verma, "Rhizoctonia solani damping-off and root rot in oilseed rape and canola" (1992) Crop Protection 11:8-13.
Khangura, R. K. et al., "Characterization and Pathogenicity of Rhizoctonia Species on Canola" (1999) Plant Disease 83:714-721.
Kim, D.-S et al. "Bacillus sp. L324-92 for Biological Control of Three Root Diseases of Wheat Grown with Reduced Tillage" (1997) Phytopathology 87(5):551-558.
Klein-Gebbinck, H.W. and D.L. Woods, "Yield Loss Assessment in Canola: Effects of Brown Girdling Root Rot and Maggot Damage on Single Plant Yield" (2002) Plant Disease 86(9):1005-1010.
Kloepper, Joseph W. et al., "Induced Systemic Resistance and Promotion of Plant Growth by Bacillus spp." (2004) Phytopathology 94(11):1259-1266.
Mazzola, M. et al., "Contribution of phenazine antibiotic biosynthesis to the ecological competence of fluorescent pseudomonads in soil habitats" (1992) Applied and Environmental Microbiology 58(8):2616-2624.

(Continued)

*Primary Examiner* — Paul Holland
(74) *Attorney, Agent, or Firm* — John D. Fado; Mark D. McNemar

(57) ABSTRACT

In exemplary embodiments, the invention provides *Pseudomonas fluorescens* 2-79 strains having pyrrolnitrin biosynthetic genes for biocontrol of soilborne diseases.

6 Claims, 3 Drawing Sheets

(56) References Cited

PUBLICATIONS

Ownley, Bonnie H., David M. Weller and Linda S. Thomashow, "Influence of in Situ and in Vitro pH on Suppression of Gaeumannomyces graminis var.Tritici by *Pseudomonas flurescens*2-79" (1992) Phytopathology 82:178-184.

Paulitz, Timothy C., Richard W. Smiley and R. James Cook, "Insights into the prevalence and management of soilborne cereal pathogens under direct seeding in the Pacific Northwest, U.S.A." (2002) Canadian Journal of Plant Pathology 24:416-428.

Formento A.N. and J. de Souza, "Overwinter and Survival of Asian Soybean Rust Caused by Phakopsora pachyrhizi in Volunteer Soybean Plants in Entre Ríos Province, Argentina" (2006) Plant Disease 90(6):826.

Pierson, Elizabeth A. and David M. Weller, "Use of Mixtures of Fluorescent Pseudomonads to Suppress Take-all and Improve the Growth of Wheat" (1994) Phytopathology 84:940-947.

Schisler, D.A. et al., "Formulation of Bacillus spp. for Biological Control of Plant Diseases" (2004) Phytopathology 94(11):1267-1271.

Tawara, S. et al., "In vitro antifungal synergism between pyrolnitrin and clotrimazole" (1989) Japan Journal of Medical Mycology 30:202-210.

Thomashow, L.S. and D.M. Weller, "Role of a phenazine antibiotic from *Pseudomonas flourescens*in biological control of Gaeumannomyces graminis var. tritici." (1988) Journal of Bacteriology 170(8):3499-3508.

Thomashow, L.S. et al., "Production of the Antibiotic Phenazine-1-Carboxylic Acid by Fluorescent Pseudomonas Species in the Rhizosphere of Wheat" Applied and Environmental Microbiology (1990) 56(4):908-912.

Timms-Wilson, T. M. et al., "Chromosomal Insertion of Phenazine-1-Carboxylic Acid Biosynthetic Pathway Enhances Efficacy of Damping-off Disease Control by *Pseudomonas fluorescens*" (2000) Molecular Plant-Microbe Interactions 13(12):1293-1300.

Weller D.M. and R.J. Cook, "Suppression of Take-All of Wheat by Seed Treatments with Fluorescent Pseudomonads" (1983) Phytopathology 73(3):463-469.

Weller, David M., "Pseudomonas Biocontrol Agents of Soilborne Pathogens: Looking Back Over 30 Years" (2007) 97(2):251-256.

Zhao, J. and J. Meng, "Detection of loci controlling seed glucosinolate content and their association with Sclerotinia resistance in Brassica napus" (2003) Plant Breeding 122:19-23.

\* cited by examiner 1 2 3 4 5 6

PSEUDOMONAS FLUORESCENS 2-79 WITH GENES FOR BIOSYNTHESIS OF PYRROLNITRIN IMPROVES BIOCONTROL ACTIVITY

REFERENCE TO RELATED APPLICATIONS

This application claims priority to U.S. Provisional Patent Application U.S. Ser. No. 61/793,784, filed Mar. 15, 2013, which is incorporated herein by reference in its entirety.

FIELD OF THE INVENTION

The invention relates to biocontrol of soilborne diseases.

BACKGROUND OF THE INVENTION

Wheat in the Pacific Northwest of the USA is damaged by one or more soilborne diseases including take-all, caused by *Gaeumannomyces graminis* var. *tritici* and *Rhizoctonia* root rot, caused by *Rhizoctonia solani* AG-8 and *R. oryzae*. These two diseases often occur as a complex in the same field and their incidence and severity are exacerbated by direct seeding (no-till) and intensive cereal production (see e.g., Paulitz, T. C., et al. 2002. Can. J. Plant Pathol. 24:416-428). Commercial wheat varieties have no resistance to either of these diseases and chemical treatments perform inconsistently (see e.g., Cook, R. J. 2003. Physiol. Mol. Plant Pathol. 62:73-86). Biological control with strains of fluorescent *Pseudomonas* spp. and *Bacillus* spp. applied as seed treatments have provided significant suppression of take-all (see e.g., Pierson, E. A., and Weller, D. M. 1994. Phytopathology 84:940-947; Weller, D. M., and Cook, R. J. 1983. Phytopathology 73:463 469) and *Rhizoctonia* root rot (see e.g., Cook, R. J., et al. 2002. Plant Dis. 86:780-784; Kim, D.-S., et al. Phytopathology 87:551-558).

Many microorganisms have been developed for commercial use and their effectiveness continues to improve (see e.g., Kloepper, J. W., et al. 2004. Phytopathology 94:1259-1266; Weller, D. M. 2007. Phytopathology 97:250-256). However, despite these successes, inconsistent performance remains a barrier to the broader use of biocontrol agents for the control of root diseases of wheat and other crops. A treatment may provide significant control in one field or season but not the next. Approaches to improve biocontrol performance have included the application of larger or multiple doses of bacterial inoculum, the development of new formulations (see e.g., Schisler, D. A., et al. 2004. Phytopathology 94:1267-1271), the use of strain combinations (see e.g., Kloepper, J. W., et al. 2004, supra; Pierson, E. A., and Weller, D. M. 1994, supra), and strain improvement by genetic engineering or the transfer of "biocontrol genes" to recipient strains with other desirable attributes (see e.g., Delany, I. R., et al. 2001. Plant Soil 232:195-205; Huang, Z., et al. 2004. FEMS Microbiol. Ecol. 49:243-251; Timms-Wilson, et al. 2000. Mol. Plant-Microbe Interact. 13:1293-1300).

Thus, what is needed in the art are improved microbial strains which provide effective and consistent biocontrol of soilborne root diseases of wheat and other crops.

Fortunately, as will be clear from the following disclosure, the present invention provides for these and other needs.

SUMMARY OF THE INVENTION

In one embodiment, the present disclosure provides a recombinant *Pseudomonas fluorescens* 2-79 comprising a stably introduced pyrrolnitrin (Prn) biosynthetic operon from *Pseudomonas fluorescens* Pf-5, wherein to the recombinant *Pseudomonas fluorescens* produces pyrrolnitrin from the biosynthetic operon. In one exemplary embodiment, the recombinant *Pseudomonas fluorescens* 2-79 has antibiotic activity against *Rhizoctonia solani*, *Rhizoctonia oryzae*, *Gaeumannomyces graminis* var. *tritici*. In another exemplary embodiment, the recombinant *Pseudomonas fluorescens* has enhanced antibiotic activity against *Gaeumannomyces graminis* var. *tritici*. In another exemplary embodiment, the recombinant *Pseudomonas fluorescens* 2-79 controls take-all and *Rhizoctonia* root rot significantly better than the parental *Pseudomonas fluorescens* strain 2-79. In another exemplary embodiment, the recombinant *Pseudomonas fluorescens* 2-79 is a member selected from the group consisting of ZHW2, ZHW6, ZHW11, ZHW14, ZHW15, ZHW18, ZHW19, ZHW23 and ZHW25. In still another exemplary embodiment, the recombinant *Pseudomonas fluorescens* 2-79 is ZHW15. In another exemplary embodiment, the recombinant *Pseudomonas fluorescens* 2-79 is ZHW25.

Other features, objects and advantages of the invention will be apparent from the detailed description which follows.

BRIEF DESCRIPTION OF THE DRAWINGS

The patent or application file contains at least one drawing executed in color. Copies of this patent or patent application publication with color drawing(s) will be provided by the Office upon request and payment of the necessary fees.

STATEMENT OF DEPOSIT

Figure 1:
FIG. 1 Thirty two recombinant colonies of 2-79 (1-32) were confirmed by PCR to contain the genes for the synthesis of Prn; NC: negative control; PC: positive control.

Strains representative of the inventions disclosed herein were deposited and accepted on Sep. 2, 2016 under the terms of the Budapest Treaty with the Agricultural Research Service (ARS) Patent Culture Collection, 1815 North University Street, Peoria, Ill. 61604. A representative *P. fluorescens* 2-79 strain transformed with genes for biosynthesis of pyrrolnitrin, otherwise referred to herein as "ZHW 15", was deposited under ARS Patent Culture Collection Reference No. NRRL 67312. A representative *P. fluorescens* 2-79 strain transformed with genes for biosynthesis of pyrrolnitrin, otherwise referred to herein as "ZHW25" was deposited under ARS Patent Culture Collection Reference No. NRRL 67313. The microorganism deposits were made under the provisions of the "Budapest Treaty on the International Recognition of the Deposit of Microorganisms for the Purposes of Patent Procedure". All restrictions on the availability to the public of these deposited microorganisms will be irrevocably removed upon issuance of a United States patent based on this application. For the purposes of this invention, any *P. fluorescens* strains having the identifying characteristics of NRRL 67312 or NRRL 67313, including subcultures and variants thereof which have the identifying characteristics and activity as described herein are included.

DETAILED DESCRIPTION OF THE INVENTION

Definitions

The term "plant" as used herein refers to whole plants, plant bodies, plant organs (e.g., leaves, stems, flowers, roots, etc.), seeds, plant tissues, plant cells and progeny of same. In an exemplary embodiment, a plant cell includes callus. In another exemplary embodiment, a plant organ includes a root, a leaf, a flower and/or the like. The term "plant" refers to the broad class of higher plants amenable to transformation techniques. The term "plant" also includes plants of any variety of ploidy levels, including polyploid, diploid, haploid and hemizygous.

The expression "stably introduced" is used herein according to standard meaning in the art. Accordingly, "stably introduced as used herein refers to a heterologous nucleic acid which has been transformed into a bacterium e.g., *Pseudomonas fluorescens* 2-79 and which following transformation has been integrated into the chromosome of the bacterium.

As used herein, the term "control" or "controlling" as in e.g., the phrase: the "controls take-all and *Rhizoctonia* root rot", or "controlling" soilborne pathogens, refers to preventing infection or infestation, reducing the severity of already infected areas or organisms, or elimination of the soil-borne diseases e.g. take-all, *Rhizoctonia solani, Rhizoctonia orzye* or other fungi or soilborne diseases whose "control" is desired.

The terms "isolated," "purified," or "biologically pure" as used herein, refer to material that is substantially or essentially free from components that normally accompany it as found in its native state. In an exemplary embodiment, purity and homogeneity are determined using analytical chemistry techniques such as polyacrylamide gel electrophoresis or high performance liquid chromatography. A nucleic acid that is the predominant species present in a preparation is substantially purified. In an exemplary embodiment, the term "purified" denotes that a nucleic acid or protein gives rise to essentially one band in an electrophoretic gel. Typically, the term "purified" means that the nucleic acid or protein is at least about 85% pure, at least about 90% pure, at least about 95% pure, or at least about 99% pure.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The term "label" as used herein, refers to a composition detectable by spectroscopic, photochemical, biochemical, immunochemical, or chemical means. Exemplary labels include $^{32}$P, fluorescent dyes, electron-dense reagents, enzymes (e.g., as commonly used in an ELISA), biotin, digoxigenin, or haptens and proteins for which antisera or monoclonal antibodies are available.

As used herein a "nucleic acid probe or oligonucleotide" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. In one exemplary embodiment, probes are directly labeled as with isotopes, chromophores, lumiphores, chromogens etc. In other exemplary embodiments probes are indirectly labeled e.g., with biotin to which a streptavidin complex may later bind. By assaying for the presence or absence of the probe, one can detect the presence or absence of the select sequence or subsequence.

Thus, the term "labeled nucleic acid probe or oligonucleotide" as used herein refers to a probe that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "primer" as used herein, refers to short nucleic acids, typically DNA oligonucleotides of at least about 15 nucleotides in length. In an exemplary embodiment, primers are annealed to a complementary target DNA strand by nucleic acid hybridization to form a hybrid between the primer and the target DNA strand. Annealed primers are then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

PCR primer pairs are typically derived from a known sequence, for example, by using computer programs intended for that purpose such as Primer (Version 0.5 ©1991, Whitehead Institute for Biomedical Research, Cambridge, Mass.). One of skill in the art will appreciate that the specificity of a particular probe or primer increases with its length. Thus, for example, a primer comprising 20 consecutive nucleotides of a sequence encoding a gene of interest will anneal to a related target sequence with a higher specificity than a corresponding primer of only 15 nucleotides. Thus, in an exemplary embodiment, greater specificity of a nucleic acid primer or probe is attained with probes and primers selected to comprise 20, 25, 30, 35, 40, 50 or more consecutive nucleotides of a selected sequence.

Nucleic acid probes and primers are readily prepared based on the nucleic acid sequences disclosed herein. Methods for preparing and using probes and primers and for labeling and guidance in the choice of labels appropriate for various purposes are discussed, e.g., in Sambrook et al., *Molecular Cloning, A Laboratory Manual* 2nd ed. 1989, Cold Spring Harbor Laboratory; and *Current Protocols in Molecular Biology*, Ausubel et al., eds., 1994, John Wiley & Sons). The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, over expressed, under expressed or not expressed at all.

The term "operably linked" refers to a functional linkage between a nucleic acid expression control sequence (such as e.g., a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" as used herein, refers to a nucleic acid construct, typically generated recombinantly or synthetically, which comprises a series of specified nucleic acid elements that permit expression of a particular nucleic acid in a host cell. The expression vector can be part of a plasmid, virus, artificial chromosome, nucleic acid fragment, or any suitable construct known in the art. Typically, an expression vector comprises a nucleic acid to be transcribed, operably linked to a promoter.

The term "transformation" as used herein encompasses any and all techniques by which a nucleic acid molecule is introduced into such a cell, including but not limited to, transfection with viral vectors, transformation with plasmid vectors, and introduction of naked DNA by electroporation, lipofection, *Agrobacterium* infection, and particle gun acceleration.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length sequence or gene sequence given in a sequence listing.

The terms "identical" or percent "identity," in the context of two or more nucleic acids or polypeptide sequences, refer to two or more sequences or subsequences that are the same or have a specified percentage of amino acid residues or nucleotides that are the same (e.g., 85% identity, 86%, 87%, 88%, 89%, 90%, 91%, 92%, 93%, 94%, 95%, 96%, 97%, 98%, 99%, or 100% identity over a specified region which may be a segment or subset of a larger sequence when compared and aligned for maximum correspondence over a comparison window, or designated region as measured using one of the following sequence comparison algorithms or by manual alignment and visual inspection. Such sequences are then said to be "substantially identical". This definition also refers to the complement of a test sequence. In an exemplary embodiment, the identity exists over a region that is at least about 25 nucleotides in length. In other exemplary embodiments, the identity exists over a region that is at least about 50-100 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395 (1984).

Another example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes below zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA). In general, two nucleic acid sequences are said to be "substantially identical" when the two molecules or their complements selectively or specifically hybridize to each other under stringent conditions.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

I. *Pseudomonas fluorescens* 2-79 with Genes for Biosynthesis of Pyrrolnitrin

A. Introduction

In one embodiment, the present disclosure provides recombinant biocontrol *Pseudomonas fluorescens* constructed by stably introducing the locus for the biosynthesis of pyrrolnitrin (Prn) from *P. fluorescens* Pf-5 into *P. fluorescens* strain 2-79, an aggressive colonizer of the roots of wheat that produces phenazine-1-carboxylic acid (PCA). Both Prn and PCA are inhibitory to soilborne pathogens. The recombinant strains produce both antibiotics in situ and suppress take-all and *Rhizoctonia* root rot significantly better as compare to the parental strain 2-79.

B. General Recombinant DNA Methods

This invention utilizes routine techniques in the field of recombinant genetics. Basic texts disclosing the general methods of use in this invention include Sambrook et al., Molecular Cloning—A Laboratory Manual (2nd Ed.), Vol. 1-3, Cold Spring Harbor Laboratory, Cold Spring Harbor, N.Y., 1989; Kriegler, Gene Transfer and Expression: A Laboratory Manual (1990); and Current Protocols in Molecular Biology (Ausubel et al., eds., 1994)). Unless otherwise noted, technical terms are used according to conventional usage. Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

This invention utilizes routine techniques in the field of microbial genetics. Basic texts disclosing the general methods and concepts used herein include e.g., *Pseudomonas*: Volume 6: Molecular Microbiology, by Juan L. Ramos, Alain Filloux (2010); Modern Microbial Genetics, Second Edition. Uldis N. Streips, Ronald E. Yasbin Ed., Wiley-Liss (2002); *Pseudomonas*: Genomics and Molecular Biology Pierre Cornelis Vrije Ed., Publisher: Caister Academic Press (2008).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized e.g., according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

The following examples are offered to illustrate, but not to limit the invention.

EXAMPLES

Example 1

Materials and Methods for Example 1

Bacterial Strains, Plasmids and Pathogens

Triparental filter mating strains: Donor strain: *Escherichia coli* DH5α(pBK-miniTn7 ΩGm-PRN) (Gmr, Ampr); Receptor strain: *P. fluorescens* strains 2-79 (Phz+) Rifr); Helper strain1: *E. coli* SM10(pUX-BF13) (Ampr); Helper strain2: *E. coli* HB101(pRK600) (Cmr).

Pathogens: *Rhizoctonia solani* AG-8 isolate C1, *Gaeumannomyces graminis* var. *tritici* (Ggt) isolate LD5 were used in laboratory and greenhouse assays.

Construction of recombinant Prn-producing derivatives of *P. fluorescens* strains 2-79: Standard methods were used for DNA isolation, restriction enzyme digestion, agarose gel electrophoresis, ligation, and transformation. The pyrrolnitrin (Prn) biosynthetic operon prnABCD from *P. fluorescens* Pf-5, was cloned previously as pBKTn7Gm-PRN (see e.g., Arima, K., et al. 1964. Agric. Biol. Chem. 28:575-576). This plasmid was transformed into *E. coli* DH5α and mobilized into *P. fluorescens* 2-79 (Phz+) (Rifr) by using a triparental filter mating technique. Transformants were selected on KMB medium supplemented with 100 µg/ml rifampicin (Rif) and 100 µg/ml gentamycin (Gen). The presence of the Prn and PCA biosynthetic genes was confirmed by PCR with Prn and PCA-gene-specific primers. Finally, growth kinetics in vitro of wild-type 2-79 and its Prn-producing recombinant derivatives were compared in ⅓×KMB broth and M9 broth (OD 600 nm) for 48 h with a TECAN Safire microplate reader.

Fungal Inhibition In Vitro

Growth inhibition of the two root pathogens by 2-79 and Prn-producing recombinant derivatives was tested on potato dextrose agar (PDA). 5 µl from an overnight culture of bacteria in KMB broth (OD600=0.1) were spotted about 1 cm from opposite edges of a PDA plate and a plug (0.5-cm diam.) cut from the leading edge of a fungal colony grown on ⅕×PDA, was placed at the center of the plate. The plates were incubated at 28° C. and the distance between the edges of the bacterial colony and the fungal mycelium was measured. For *G. graminis* var. *tritici*, the bacteria were spotted 24 h after introduction of the fungus and the zone of inhibition was measured 5 d later. For *R. solani* AG-8 and *R. solani* AG2-1, the bacteria and the fungus were introduced at the same time and the inhibition zone was measured after 5 d.

Seed Treatment

Spring wheat (cv. Penawawa) and canola (cv. InVigor 8440) were coated with bacteria (approximately $10^7$ per seed) by using the methods described by Pierson and Weller (8). Bacterial inoculum was grown on KMB agar plates for 48 h at 27° C. Cells were scraped from the plates, suspended in sterile water, washed twice by centrifugation for 3 min (14,000 rpm), and diluted to give the appropriate bacterial concentration. Methylcellulose (2%) was added to the bacterial suspension and seeds were coated with the suspension, mixed, and air-dried overnight in a laminar flow hood. The actual number of CFU per seed was determined by dilution plating on KMB immediately before planting.

Disease Suppression Assays

Tube assays were used to test the biocontrol activity of the parental and recombinant strains against take-all and *Rhizoctonia* root rot. Pathogen inoculum was prepared by growing each pathogen on autoclaved whole oat grains. The colonized grains were stored at 4° C. until used. Plastic tapered tubes (2.5 cm×20 cm) with holes at the bottom were plugged with cotton balls, and then filled to a height of about 3 cm with fine vermiculite followed by 10 g of Quincy virgin soil (non-cropped Shano sandy loam), with or without inoculum of a pathogen. For biocontrol assays of take-all and *Rhizoctonia* root rot, the soil was amended with 0.7% (w/w) (for *R. solani* AG2-1, the dosage is 0.1%) of freshly ground oat-kernel inoculum (sieved to collect particle sizes of 0.25-0.50 mm), and each tube received 10 ml of water amended with metalaxyl (0.6 g/8 L) to minimize interference by *Pythium* spp., which are indigenous in soils of the Pacific Northwest. For take-all suppression assays, the tubes were seeded immediately and for *Rhizoctonia* suppression assays the tubes were seeded after incubation at room temperature for 48 h. Three wheat seeds were sown per tube and covered with about 5 ml of vermiculite. The tubes were arranged in a randomized complete block design and incubated in a growth chamber for three weeks (12-h photoperiod, 16° C.). After seedling emergence (3-4 d), each tube was watered three times weekly and one of those times with 10 ml of one-third-strength Hoagland's solution. Each treatment was replicated five times with 5 tubes per replicate. *Rhizoctonia* root rot and take-all in wheat were evaluated by determining disease severity on a scale of 0-8 and by measuring plant height. Results of *Rhizoctonia solani* AG2-1 in canola were evaluated by determined post-emergence damping-off, shoot dry weight, root dry length and shoot length. All experiments were conducted two times with similar results.

Detached-Leaf assays

Leaves of canola were sprayed with bacteria (1 mL each leaf), and 24 h later inoculated with *Sclerotinia sclerotiorum* WM-A1 by placing a mycelia plug (diam.=0.5 cm) on the leaf. The detached leaves of canola were put into culture dishes on filter paper moistened with water and incubated at 22° C. room. The area of hyphal growth on each detached leaf was recorded after 4 days and 6 days of incubation. Each strain (treatment) had 9 replicates. Five treatments needed 45 leaves. The experiment was performed two times. Totally, 90 leaves were needed.

Measured lengths of the long axis and shoot axis were averaged and the hyphal growth radius was determined using the formula: Area=JI (radius)$^2$ as known in the art (see e.g., Hu, X., et al. 2005. Appl. Microbiol. Biotechnol. 68:802-807).

$$\text{Inhibition rate (\%)} = \frac{CK \text{ hyphal growth area } (cm^2) - \text{treatment hyphal growth area } (cm^2)}{CK \text{ hyphal growth area } (cm^2)} \times 100\%$$

Antibiotic Identification

Bacteria were incubated on LB agar+2% glucose at 28° C. for 66 hrs. The agar was extracted with acetone and chloroform. The crude extracts and purified preparations were analyzed by thin-layer chromatography (TLC) with (Silica Gel GHLF) plate and chloroform-hexane (4:1, vol/vol). Visualization was performed by exposing to air for 10 min. and monitoring at 254 nm.

Colonization of the wheat rhizosphere by fluorescent *Pseudomonas* spp. Wheat seed was treated with bacterial strains at $10^5$ CFU/seed, planted, and grown as described above. Population sizes of the introduced strains in the rhizosphere were determined after 3, 6, 9 weeks as described by Landa et al. (2002) Phytopathology 92:129-137. Briefly, six seedlings were selected at random from each replicate and shaken to remove the loosely-adhering soil. One gram of roots with associated soil was suspended in 10 ml of sterile water in a 50-mL screw-cap centrifuge tube, agitated vigorously by Vortex mixing and then sonicated in and ultrasonic cleaner, and serial dilutions of the wash suspension were made using 96-well microliter plates with each well filled with 2 μL of sterile water. After all dilutions were made, 50 μl of each dilutions was transferred to wells of a 96-well microliter plate filled with ⅓×KMB broth containing rifampicin and cycloheximide (each at 100 μg/mL), chloramphenicol (13 μg/mL), and ampicillin (40 μg/mL). Optical density at OD600 were measured after 72 h to determine if growth occurred.

Statistical Analysis

Colonization experiments were arranged in a randomized complete block design, and data were analyzed with STATISTIX 8.0 software (Analytical Software, St. Paul, Minn., USA). Population data were converted to log CFU $g^{-1}$ fresh root weight. Differences in population densities, root disease, or plant height among treatments were determined by standard analysis of variance and mean comparisons among treatments were performed by using Fisher's protected least significant difference test (LSD) ($P=0.05$) or by the Kruskal-Wallis test ($P=0.05$).

Results for Example 1

Selection and characterization in vitro of recombinant strains. Mating of *P. fluorescens* 2-79 with *E. coli* DH5α (pBK-miniTn7 ΩGm-PRN) (Gmr, Ampr) yielded thirty-two recombinant colonies, nine of which successfully survived selection on M9 agar containing kanamycin. These clones, designated ZHW2, ZHW6, ZHW11, ZHW14, ZHW15, ZHW18, ZHW19, ZHW23, ZHW25, remained rifampicin and gentamycin-resistant after several successive transfers on KMB agar and were stable with regard to colony size, morphology, color. The presence of the introduced pyrrolnitrin biosynthetic genes was confirmed by PCR with the pyrrolnitrin-specific primers Prn1 and Prn seq2 (FIG. 1).

Figure 2:
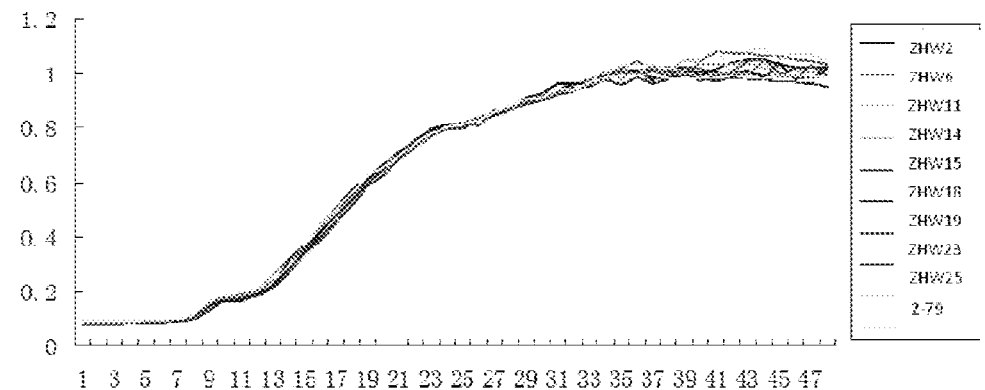
FIG. 2 Growth rate of *P. fluorescens* 2-79 and its Prn recombinant strains in ⅓× KMB broth.
Figure 3:
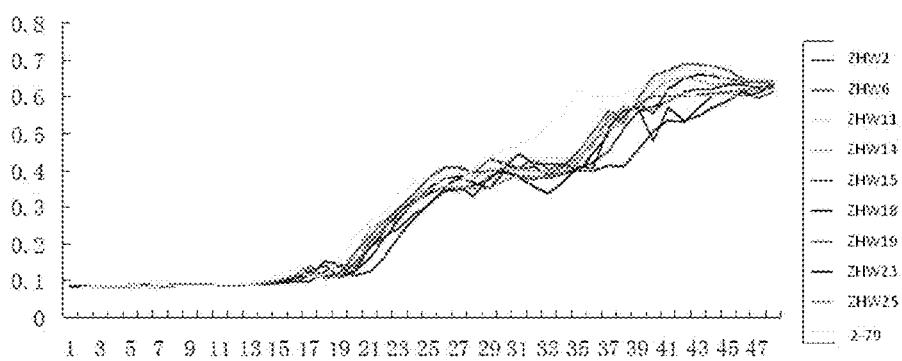
FIG. 3 Growth rate of *P. fluorescens* 2-79 and its PRN recombinant strains in M9 medium.

Tests of growth rate for nine recombinant strains and 2-79 in ⅓×KMB broth and M9 broth showed that similar results were obtained when the experiment was performed in ⅓× KMB broth between nine recombinant strains and 2-79 (FIG. 2). In M9 broth, most times the growth rate was similar between the nine recombinant strains and 2-79 except from 29-40 h when the density of strain 2-79 was higher than that of nine recombinant strains (FIG. 3). All of the recombinant strains produced larger zones of inhibition against the two fungal pathogens than did strain 2-79. Inhibition of *G. graminis* var. *tritici* by the recombinant strains was 60-73% greater than that by 2-79, and the recombinant strains have good inhibition of *R. solani* AG-8, however the parental strain 2-79 had no inhibition of *R. solani* AG-8 (Table 1).

TABLE 1

Inhibition in vitro of wheat root pathogens by 2-79 and recombinant derivatives

| | Zone of inhibition (cm)$^a$ | |
| --- | --- | --- |
| Strain | *Gaeumannomyces graminis* var. *tritici* LD5 | *R. solani* AG-8 |
| ZHW2 | 0.50a | 1.55ab |
| ZHW6 | 0.40a | 1.55ab |

TABLE 1-continued

Inhibition in vitro of wheat root pathogens
by 2-79 and recombinant derivatives

| | Zone of inhibition (cm)[a] | |
|---|---|---|
| Strain | Gaeumannomyces graminis var. tritici LD5 | R. solani AG-8 |
| ZHW11 | 0.50a | 1.5b |
| ZHW14 | 0.38ab | 1.55ab |
| ZHW15 | 0.55a | 1.6a |
| ZHW18 | 0.48a | 1.5b |
| ZHW19 | 0.45a | 1.6a |
| ZHW23 | 0.50a | 1.55ab |
| ZHW25 | 0.55a | 1.6a |
| 2-79 | 0.15b | 0c |

[a]Width of the zone of inhibition was measured from the edge of the fungal colony to the edge of the bacterial colony. Means followed by the same letter are not significantly different (P = 0.05)

The recombinant strains had good inhibition of *R. solani* AG2-1, but the parental strain 2-79 had weak inhibition of *R. solani* AG2-1 (P<0.05). Zones of inhibition against *S. sclerotiorum* WM-A1 by 2-79 and the recombinant strains had no significant difference (P>0.05), but two recombinant strains ZHW15 and ZHW25 produced larger zones of inhibition than did 2-79 (Table 2).

TABLE 2

Inhibition in vitro of canola pathogens by 2-79 and
recombinant derivative strains

| | Zone of inhibition (cm)[A] | |
|---|---|---|
| Strain | R. solani AG2-1 | S. sclerotiorum WM-A1 |
| ZHW15 | 0.53a[B] | 1.63a |
| ZHW25 | 0.65a | 1.86a |
| 2-79 | 0.1b | 1.3a |

Figure 4:
FIG. 4. Thin-layer chromatography (TLC) of 2-79 and recombinant derivative strains. 1. Prn standard; 2. 2-79 wild type; 3. ZHW2; 4. ZHW6; 5. ZHW15; 6. ZHW25; 7. PCA standard

[A]Width of the zone of inhibition was measured from the edge of the fungal colony to the edge of the bacterial colony.
[B]Means in the same column followed by the same letter are not significantly different at P = 0.05 according to the protected LSD The recombinant strains had enhanced inhibition of *G. graminis* var. *tritici* LD5 as compared to the parental strain 2-79 and increased inhibition of *R. solani* AG-8. TLC results showed that cultures of the recombinant strains produced both Prn and PCA in vitro, but the wild type 2-79 could not produce Prn (FIG. 4).

Root disease suppression in soil. Bacteria were applied at doses of $10^7$ CFU per seed. *P. fluorecens* 2-79 and the recombinant strains ZHW15 and ZHW25 (used as examples of the recombinant strains constructed) provided significant (P=0.05) suppression of take-all as compared to the non-treated take-all (Ggt isolate LD5) control and the non-treated take-all (Ggt isolate LD5)+1% methyl cellulose (MC) control based on root disease ratings. The recombinant strains provided significantly more control than 2-79. ZHW15 and ZHW25 reduced the disease rating, and they were significantly different (P=0.05) as compared to the wild-type 2-79. The shoot length was not significantly different (P=0.05) among the wild type 2-79, the two recombinant strains, the nontreated LD5 control, and the nontreated 1% MC+LD5 control (Table 3).

TABLE 3

Suppression of take-all of wheat by *P. fluorescens* 2-79
and recombinant strains

| Treatment | Rating | Shoot length (mm) |
|---|---|---|
| Blank control (no *Pseudomonas*, No take-all, no Ggt LD5) | 0.1286 ± 0.3777 e[z] | 23.42 ± 2.4771a |
| 1% MC + take-all (Ggt LD5 control) | 4.8108 ± 1.5499 a | 16.030 ± 2.1575c |
| Take-all (isolate LDS) control | 4.1467 ± 1.4950 ab | 16.011 ± 2.3554c |
| 2-79 | 3.7200 ± 1.1574 bc | 16.092 ± 2.2777c |
| ZHW15 | 2.8333 ± 1.0070 d | 16.147 ± 2.9042c |
| ZHW25 | 2.6986 ± 1.0889 d | 16.363 ± 1.9393c |

[z]Means followed by the same letter are not significantly different (P = 0.05).

The two recombinant strains significantly (P=0.05) also reduced the disease rating of roots with symptoms caused by *Rhizoctonia solani* as compared to the nontreated *Rhizoctonia* control and the nontreated 1% MC+*Rhizoctonia* control. Shoot length of the two recombinants were higher than that of the nontreated *Rhizoctonia* control and the nontreated 1% MC+*Rhizoctonia* control, but there is no significant different in shoot length with that of wild type 2-79. The shoot length had no significant difference (P=0.05) among the wild type, two recombinant strains, the nontreated *Rhizoctonia* control and the nontreated 1% MC+*Rhizoctonia* control (Table 4).

TABLE 4

Suppression of *Rhizoctonia* root rot in wheat
by 2-79 and recombinant strains

| Treatment | Rating | Shoot length (mm) |
|---|---|---|
| Blank control (no *Pseudomonas*, no *Rhizoctonia*) | 0.1831 ± 0.4873 d[z] | 19.915 ± 2.0324 a |
| 1% MC + *Rhizoctonia* control | 4.3143 ± 0.9712 a | 15.983 ± 2.5116 d |
| *Rhizoctonia* control | 4.7162 ± 0.9865 a | 16.455 ± 2.7587 bc |
| 2-79 | 2.8082 ± 0.6802 b | 17.395 ± 2.6632 b |
| ZHW15 | 1.5676 ± 0.9375 c | 17.047 ± 2.4277 bc |
| ZHW25 | 1.7887 ± 1.0812 c | 16.977 ± 2.5747 bc |

The results from suppression of *Rhizoctonia* root rot in canola by 2-79 and recombinant strains are shown in Table 5.

TABLE 5

Suppression of *Rhizoctonia* root rot on Canola by 2-79 and recombinant strains

| Treatment | Damping-off (%) | Shoot dry weight[x] (g) | Root dry weight[x] (g) | Shoot length[x] (cm) |
|---|---|---|---|---|
| Blank control (no *Pseudomonas*, no *Rhizoctonia*) | 0 | 0.0470 ± 2.582E−03a[z] | 0.0117 ± 1.337E−03a | 75.00 ± 4.08a |
| 1% MC + *Rhizoctonia* control | 94.4 | — | — | — |
| *Rhizoctonia* control | 100 | — | — | — |
| 2-79 | 35.4 | 0.0260 ± 2.608E−03c | 0.0063 ± 1.211E−03c | 53.83 ± 1.47d |

TABLE 5-continued

Suppression of *Rhizoctonia* root rot on Canola by 2-79 and recombinant strains

| Treatment | Damping-off (%) | Shoot dry weight[x] (g) | Root dry weight[x] (g) | Shoot length[x] (cm) |
|---|---|---|---|---|
| ZHW15 | 15.1 | 0.0310 ± 2.739E–03b | 0.0080 ± 1.224E–03b | 60.00 ± 2.73c |
| ZHW25 | 18.1 | 0.0271 ± 1.457E–03c | 0.0070 ± 1.309E–03bc | 65.00 ± 2.00b |

[z]Means followed by the same letter are not significantly different (P = 0.05).
[x]Means the weight or length of each 10 Canola.

There was 94.4% and 100% post-emergence seedling damping-off in 1% MC+*Rhizoctonia* control and nontreated *Rhizoctonia* control, respectively. There was obvious decrease of post-emergence seedling damping-off in 2-79 and the two recombinant strains as compared to nontreated controls. But damping-off of two recombinant strains ZHW15 and ZHW25 was 2.3 and 2.0 times lower than that of the parental strain 2-79.

Inhibition of *S. sclerotiorum* WM-A1 in detached leaves showed there were no significant differences (P=0.05) among the wild type, ZHW15 and ZHW25, but the areas of *S. sclerotiorum* WM-A1 hyphal growth with ZHW25 was smaller than that of 2-79 (Table 6).

TABLE 6

Inhibition of *S. sclerotiorum* WM-A1 in detached leaves

| Treatment | Areas of *S. sclerotiorum* WM-A1 hyphal growth (cm$^2$) |
|---|---|
| CK | 3.88 ± 0.76a[A] |
| 2-79 | 1.30 ± 0.96b |
| ZHW15 | 1.30 ± 0.77b |
| ZHW25 | 0.59 ± 0.49b |

[A]Means followed by the same letter are not significantly different (P = 0.05).

Colonization in the wheat rhizosphere. Strains 2-79, ZHW15 and ZHW25 applied at $10^5$ CFU per seed multiplied rapidly on the seeds and in the wheat rhizosphere. The population sizes of all of the strains increased about 1000-fold on the seed coat and the radical by cycle 1 (three weeks). 2-79 wild type and ZHW25 peaked at cycle 1; ZH15 peaked at cycle 2. Populations of the recombinant strains and 2-79 did not differ in size throughout the three cycles (Table 7).

TABLE 7

Population density of introduced wild-type and the recombinant strains on the roots of wheat (cv. penawawa)

| | Mean population density | | |
|---|---|---|---|
| Cycle | 2-79 wild type | ZHW15 | ZHW25 |
| 1 | $1.594 \times 10^7$a[A] | $1.349 \times 10^7$a | $1.480 \times 10^7$a |
| 2 | $0.738 \times 10^7$a | $2.754 \times 10^7$a | $1.004 \times 10^7$a |
| 3 | $1.500 \times 10^6$a | $6.801 \times 10^6$a | $1.166 \times 10^6$a |

[A]Means in the same column followed by the same letter are not significantly different at P = 0.05 according to the protected LSD.

DISCUSSION

A variety of soil-borne pathogens such as *R. solani* AG8 and *G. graminis* usually exist in the same wheat field as a complex. In oilseed rape (canola), *R. solani* AG2-1 and *S. sclerotiorum* are both serious pathogens. A few fluorescent *Pseudomonas* spp. strains can suppress these pathogens individually but, no single strain is effective against all four phytopathogens. Thus, what is needed in the art are strains which can provide biological control against a wider range of wheat and canola soil-borne pathogens and diseases.

The recombinant strains of 2-79 disclosed herein are the first examples wherein the prnABCD gene cluster has been successfully introduced into wild-type 2-79 giving those strains the ability to produce pyrrolnitrin in addition to phenazine-1-carboxylic acid which is naturally produced by strain 2-79. Even though bacteria that produce both antibiotics are found in nature such as *P. chlororaphis* subsp. *aureofaciens* 30-84, their ability against *G. graminis* and *R. solani* is weaker than that of recombinant derivatives of 2-79 (Data not shown).

Introduction of the constitutively expressed Prn biosynthetic genes did not bring a metabolic burden on 2-79 because all of the recombinant strains grew as fast as the parent strain in ⅓×KMB. Furthermore, 2-79 and its recombinant derivatives had similar population dynamics throughout the three cycle-colonization experiment.

*P. fluoresens* 2-79 is suppressive to take-all of wheat caused by *G. graminis* var. *tritici*. Production of the antibiotic phenazine-1-carboxylic acid (PCA) is the main mechanism of action against take-all root disease of wheat by this strain (see e.g., Ownley, B. H., et al. 1992. Phytopthology. 82:178-184). In vitro and in vivo, recombinant strains provided obviously greater suppression of *G. graminis*, even though *G. graminis* is sensitive to the phenazine produced by wild-type 2-79. Furthermore, introduction of ability to produce pyrrolnitrin enhanced the capacity of 2-79 against take-all as well. Introduction of ability to produce pyrrolnitrin to 2-79 also increased its spectrum of activity and made 2-79 gain the capacity to control *R. solani* AG-8 on wheat and *R. solani* AG-2-1 on canola.

Pyrrolnitrin (3-chloro-4-(2'-nitro-3'-chlorophenyl)-pyrrole) is an antibiotic with broad-spectrum antifungal activity which was first isolated from *Pseudomonas pyrrocinia*. The prnABCD gene cluster from *Pseudomonas fluorescens* encodes the biosynthetic pathway for pyrrolnitrin, a secondary metabolite derived from tryptophan which has strong anti-fungal activity (see e.g., Hammer P. E., et al. 1999. FEMS Microbiol. Lett. 180:39-44).

Our results indicate 2-79 transgenic strains disclosed herein provide a better choice for control of soilborne pathogens.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A recombinant *Pseudomonas fluorescens* 2-79 strain comprising a stably transformed pyrrolnitrin (Prn) biosynthetic operon from *Pseudomonas fluorescens* Pf-5, wherein said recombinant *Pseudomonas fluorescens* 2-79 strain produces pyrrolnitrin from said Prn biosynthetic operon and wherein said recombinant *Pseudomonas fluorescens* 2-79 strain is a member selected from the group consisting of the recombinant *Pseudomonas fluorescens* 2-79 strains deposited under Reference Nos: NRRL 67312 and NRRL 67313.

2. The recombinant *Pseudomonas fluorescens* 2-79 strain of claim 1, wherein said recombinant *Pseudomonas fluorescens* 2-79 strain has antibiotic activity against *Rhizoctonia solani, Rhizoctonia oryzae, Gaeumannomyces graminis* var, *tritici*, or a combination thereof.

3. The recombinant *Pseudomonas fluorescens* 2-79 strain of claim 2, wherein said recombinant *Pseudomonas fluorescens* strain has enhanced antibiotic activity against *Gaeumannomyces graminis* var, *tritici* as compared to a parental *Pseudomonas fluorescens* 2-79 strain.

4. The recombinant *Pseudomonas fluorescens* 2-79 strain of claim 1, wherein said recombinant *Pseudomonas fluorescens* 2-79 strain controls take-all and *Rhizocotonia* root rot significantly better than a parental *Pseudomonas fluorescens* 2-79 strain.

5. The recombinant *Pseudomonas fluorescens* 2-79 strain of claim 1, wherein said recombinant *Pseudomonas fluorescens* 2-79 strain is the strain deposited under Reference No. NRRL 67312.

6. The recombinant *Pseudomonas fluorescens* 2-79 of claim 1, wherein said recombinant *Pseudomonas fluorescens* 2-79 strain is the strain deposited under Reference No. NRRL 67313.

\* \* \* \* \*

UNITED STATES PATENT AND TRADEMARK OFFICE
CERTIFICATE OF CORRECTION

PATENT NO. : 9,528,115 B1  
APPLICATION NO. : 14/208543  
DATED : December 27, 2016  
INVENTOR(S) : David M. Weller et al.

Page 1 of 1

It is certified that error appears in the above-identified patent and that said Letters Patent is hereby corrected as shown below:

Correct Title from "PSEUDOMONAS FLUORESCENS2-79 WITH GENES FOR BIOSYNTHESIS OF PYRROLNITRIN IMPROVES BIOCONTROL ACTIVITY" to "PSEUDOMONAS FLUORESCENS 2-79 WITH GENES FOR BIOSYNTHESIS OF PYRROLNITRIN IMPROVES BIOCONTROL ACTIVITY."

Signed and Sealed this  
Ninth Day of May, 2017

Michelle K. Lee  
*Director of the United States Patent and Trademark Office*